United States Patent [19]
Winters

[11] Patent Number: 4,984,532
[45] Date of Patent: Jan. 15, 1991

[54] APPARATUS FOR CONTROLLING THE SPEED AND IMPRESSION ON A MANUAL INK PROOFER

[76] Inventor: Carey Winters, 401 Forty Oaks Farm Rd., West Monroe, La. 71297

[21] Appl. No.: 397,257

[22] Filed: Aug. 23, 1989

[51] Int. Cl.$^5$ .......................................... G01N 33/32
[52] U.S. Cl. .............................. 118/242; 73/150 R; 118/248; 118/258; 118/713
[58] Field of Search .................. 118/71, 242, 248, 258, 118/261, 713; 73/150 R; 101/269, 359

[56] References Cited

U.S. PATENT DOCUMENTS

| | | | |
|---|---|---|---|
| 1,691,739 | 11/1928 | Schur | 73/150 R |
| 2,167,652 | 8/1939 | Hoch | 73/150 R |
| 2,349,699 | 5/1944 | Boor | 73/150 R |
| 2,353,852 | 7/1944 | Rowland et al. | 73/150 R |
| 2,705,424 | 4/1955 | Pomper | 73/150 R |
| 2,990,715 | 7/1961 | Bradt | 73/150 R |
| 3,436,963 | 4/1969 | Domen, Sr. | 73/150 R |
| 3,675,476 | 7/1972 | Zapfe | 73/150 R |
| 4,258,125 | 3/1981 | Edhlund | 118/261 |
| 4,522,057 | 6/1985 | Kerchiss | 73/150 R |
| 4,541,273 | 9/1985 | Bery | 73/150 R |
| 4,852,486 | 8/1989 | Ely et al. | 101/145 |

FOREIGN PATENT DOCUMENTS

| | | | |
|---|---|---|---|
| 3409961 | 9/1985 | Fed. Rep. of Germany | 73/150 R |
| 2270571 | 12/1975 | France | 73/150 R |
| 476520 | 12/1937 | United Kingdom | 73/150 R |

OTHER PUBLICATIONS

Gardner Laboratory, Inc. brochure, "Instruments for Measuring", Bethesda, Md., Physical Test Bulletin, Oct. 1964, pp. 1-9.

Primary Examiner—James C. Housel
Attorney, Agent, or Firm—Brady, O'Boyle & Gates

[57] ABSTRACT

Apparatus for controlling the speed and impression on a manual ink proofer engaging a substrate wherein the manual ink proofer is detachably connected to a piston rod of a fluid motor. A valve is provided for controlling the speed at which the piston rod and associated ink proofer is retracted toward the cylinder, and an adjustable downward pressure is applied to the ink proofer to obtain the desired impression pressure.

8 Claims, 1 Drawing Sheet

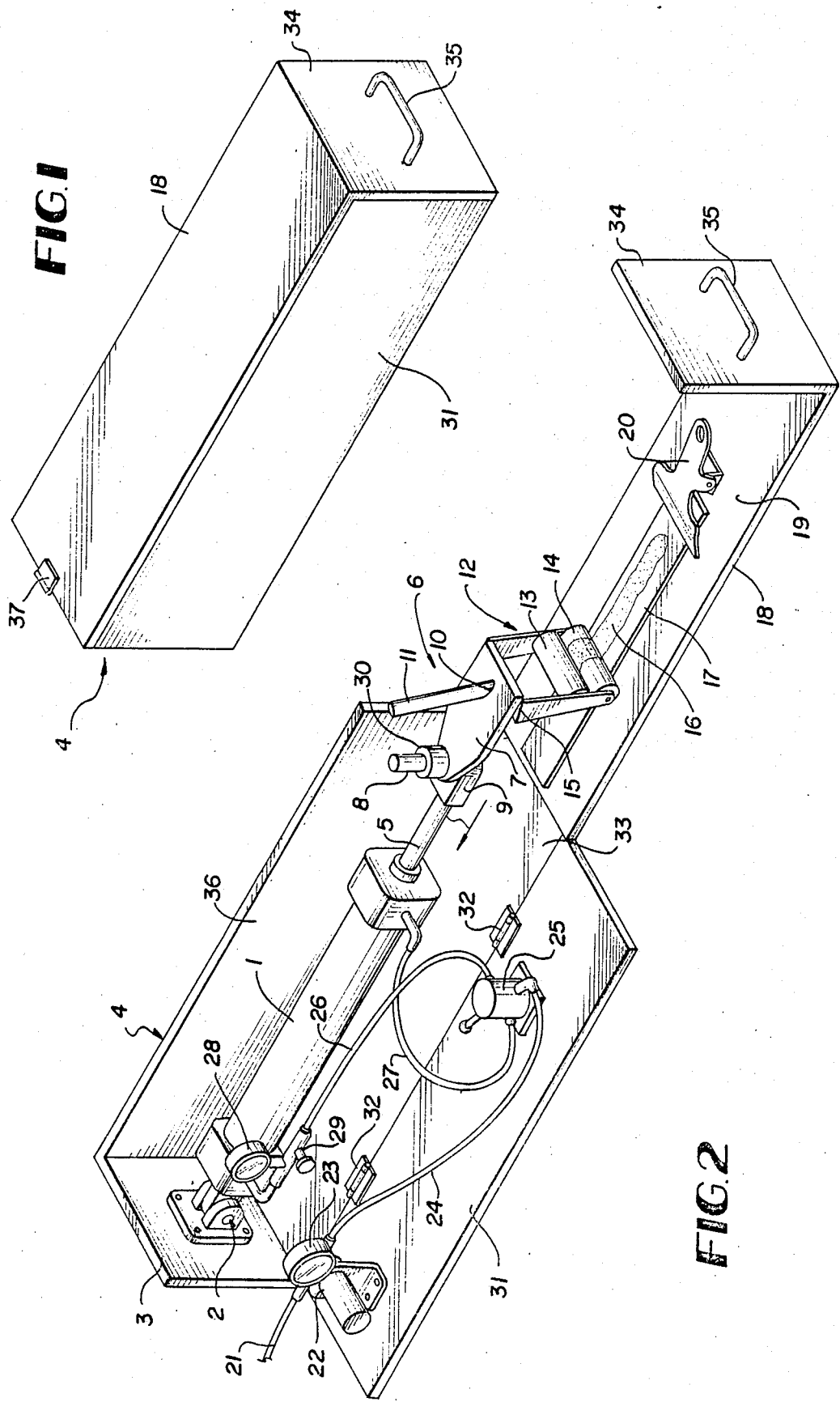

APPARATUS FOR CONTROLLING THE SPEED AND IMPRESSION ON A MANUAL INK PROOFER

BACKGROUND OF THE INVENTION

Manual ink proofers of the type disclosed in U.S. Pat. No. 2,990,715 to Bradt dated July 4, 1961 are employed for proofing ink colors in order to accurately predict the results to be obtained by running a selected ink specimen in a printing press.

In flexographic printing, wherein rubber plates are employed for delivering the ink to the stock or paper to be printed, the flexographic ink technician is given an ink specimen which has been determined to be acceptable for use on a particular press, and a production run sample, to be used as the standard for color and density.

One of the most difficult tasks facing a flexographic ink technician is proofing an ink in a manner so that the color will duplicate the color of the production run sample from the flexographic printing press. It is common knowledge to those skilled in the art that if three trained technicians pull a proof, using the same ink on the same hand proofer, three different color shades will result.

Color shade on a flexographic printing press is dependent on the ink film thickness applied to the substrate or stock. The ink film thickness is determined by the speed of the press, the pressure applied between the printing plate and paper; viz., impression, and the pressure between the rollers on the printing unit. Similarly, color shade on a flexographic hand proofer is also dependent on the ink film thickness applied to the substrate which thickness is determined by the speed at which the technician pulls the hand proofer across the substrate, and the impression pressure the technician applies to the proofer while moving it across the substrate. Thus, the speed and impression is totally dependent on the manual skill of the flexographic ink technician, while the only variable not controlled by the technician is the pressure between the ink roller and transfer roller of the manual proofer.

To overcome the disadvantages experienced by manually pulling a proof, the apparatus of the present invention has been devised which comprises, essentially, a fluid motor including a cylinder and piston rod upon which a conventional manual proofer is operatively connected. A valve is provided for controlling the speed at which the piston rod is retracted into the cylinder and concomitantly the proofer on the substrate; and variable pressure means is applied to the proofer to obtain the desired impression pressure. By this construction and arrangement, the speed, impression and roller pressure are completely controlled by the technician, whereby the same ink color will be duplicated each time the apparatus is used.

Each make and model of flexographic presses tend to apply different ink film thicknesses. On any single flexographic press, each print station, sometimes as many as ten, can apply different ink film thicknesses. By calibrating the apparatus of the present invention to a given press and/or unit, the color control problem between ink producer and press can be virtually eliminated.

BRIEF DESCRIPTION OF THE DRAWING

FIG. 1 is a perspective view of the carrying case enclosing the apparatus of the present invention; and FIG. 2 is a perspective view of the carrying case in the open position showing the various components of the apparatus of the present invention.

DESCRIPTION OF THE PREFERRED EMBODIMENT

Referring to the drawing and more particularly to FIG. 2, the apparatus of the present invention comprises a pneumatic cylinder 1 having one end pivotally connected as at 2 to an end wall 3 of a carrying case 4. A reciprocatory piston rod 5 is mounted in the cylinder and extends outwardly through the opposite end thereof. A carriage 6 is connected to the free end of the piston rod 5 and comprises a plate 7 connected to the piston rod by a bolt 8 extending through the piston rod head 9 upwardly through the plate 7. The outer end of the plate 7 is provided with an inclined aperture 10 for receiving the inclined handle 11 of a conventional hand proofer 12 which includes an ink roller 13 and a transfer roller 14 rotatably mounted in a bifurcated arm 15 connected to the handle 11.

The transfer roller 14 is adapted to apply an ink specimen 16 to a substrate 17 held on the carrying case wall 18, having a rubber interior surface 19, by a spring clip 20 secured thereto.

The pneumatic system for controlling the extension and retraction of the piston rod 5 comprises a compressed air supply line 21 detachably connected and communicating with a pressure regulator 22 having a gauge 23. Another air line 24 extends from the pressure regulator 22 to a manually controlled rotary valve 25. Additional air lines 26 and 27 are respectively connected between opposite ends of the cylinder and the rotary valve 25, whereby the piston rod 5 can be extended and retracted by manipulating the valve 25. The line 26 is provided with a pressure gauge 28 and a manually controlled vent valve 29 whereby the compressed air being exhausted from the cylinder 1 during the retraction of the piston rod 5 can be controlled, to thereby vary the speed of retraction of the piston rod and associated proofer 12.

To apply a predetermined impression on the proofer 12 and substrate 17, an adjustable downward pressure is applied to the carriage plate 7. This is accomplished in the illustrated apparatus by applying weights 30 to the bolt 8. It is contemplated that other means may be employed for obtaining the desired adjustable downward pressure, for instance, employing a pneumatic actuated piston engaging the top surface of the carriage plate 7.

To complete the structural description of the apparatus of the present invention, the regulator 22 and gauge 23, and valve 25, are secured to a wall 31 of the carrying case 4, the wall 31 being hingedly connected as at 32 to the side edge of another wall 33 of the carrying case. The wall 18 of the carrying case is provided with an integral end wall 34 having a carrying handle 35. To enclose the apparatus in the carrying case 4, the wall 31 is folded upwardly, and the wall 18 and associated end wall 34 are turned upside down and placed on the top edges of wall 31 and wall 36. A suitable latch 37 is provided on the end wall 3 for holding the carrying case in the closed position.

In using the apparatus of the present invention, the carrying case 4 is opened as shown in FIG. 4, and the carrying case wall 18 having the rubber surface 19 facing up is placed in front and in alignment with the carriage 6. The rotary valve 25 is moved to a position communicating air line 24 with air line 27 so that the piston rod 5 will be moved to the "IN" or retracted position. The compressed air line 21 from an air supply source of 90 psi is connected to the pressure regulator which is set to provide a system working pressure of 80 psi. A 2½"×12" piece of the desired substrate 17 is secured to the rubber surface 19 by spring clip 20. Rotary valve 25 is then moved to a position wherein the incoming compressed air in line 24 is placed in communication with air line 26, to thereby extend the piston rod 5 and associated carriage 6 to the "OUT" position. The hand proofer 12 is then attached to the carriage 6 by pivoting the cylinder 1 upwardly about the pivot connection 2, and inserting the proofer handle 11 upwardly through the inclined aperture 10 in the carriage 6. When the piston 5 and associated carriage 6 and hand proofer 12 are moved downwardly, the transfer roller 14 will engage the substrate 17. A small quantity of ink is deposited on the ink roller 13 and the valve 25 is then moved to the "IN" position causing the carriage 6 and associated hand proofer 12 to be drawn toward the pneumatic cylinder 1, to thereby produce a printed ink sample 17.

Printed results can accurately and consistently be affected by the addition or subtraction of weights 30, to thereby increase or decrease the impression pressure of the hand proofer 12 in relation to the substrate 17 at the point of engagement which is also the point of ink transfer. Similarly, printed results can be accurately and consistently affected by the speed at which the carriage 6 and associated hand proofer 12 move to the "IN" position by manipulating the vent valve 29.

From the above description, it will be appreciated by those skilled in the art that by means of the apparatus of the present invention, the speed, impression and roller pressure of the manual ink proofer 12 are completely controlled by the ink technician; whereby the same ink color will be duplicated each time the apparatus is used.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. Apparatus for ink proofing comprising an ink proofer and means for controlling the speed and impression on said ink proofer, said ink proofer having a bifurcated arm, a roller rotatably mounted in said arm and adapted to engage a substrate, and a handle secured to said bifurcated arm, said controlling means comprising a motor, a carriage, means connected between said motor and said carriage for transferring reciprocatory movement to said carriage, the handle of said ink proofer being detachably connected to said carriage, means operatively connected to said carriage for adjusting the downward pressure on the carriage to thereby apply a predetermined impression on the ink proofer, and means operatively connected to the motor for varying the speed of retraction of the carriage.

2. Apparatus according to claim 1, wherein the motor comprises a pneumatic cylinder and a reciprocatory piston rod.

3. Apparatus according to claim 2, wherein valve means is connected between a source of compressed air and the pneumatic cylinder for controlling the direction of air flow into the cylinder for reciprocating said piston rod.

4. Apparatus according to claim 3, wherein said carriage speed varying means includes a vent valve means operatively connected to the pneumatic cylinder for controlling the speed of retraction of the piston rod and associated carriage and ink proofer.

5. Apparatus according to claim 4, wherein said downward pressure adjusting means includes weights detachably connected to the carriage for adjusting the downward pressure thereon.

6. Apparatus for controlling the speed and impression on an ink proofer having a bifurcated arm, a roller rotatably mounted in said arm and adapted to engage a substrate, and a handle secured to said bifurcated arm, said apparatus comprising a pneumatic cylinder an a reciprocatory piston rod slidably mounted in said cylinder, a carriage connected to the outer end of said piston rod, whereby reciprocatory movement produced by the pneumatic cylinder is transferred to the carriage, means for detachably connecting the handle of said ink proofer to said carriage, a base support, one end of said pneumatic cylinder being pivotally connected to said base support to thereby facilitate the connecting of the ink proofer handle to the carriage, means operatively connected to said carriage for adjusting the downward pressure on the carriage to thereby apply a predetermined impression on the ink proofer, and means operatively connected to the pneumatic cylinder for varying the speed of retraction of the carriage.

7. Apparatus according to claim 6, wherein said carriage comprises a plate having an aperture therein, said handle extending upwardly through the aperture in said plate.

8. Apparatus according to claim 7, wherein a carrying case is provided for enclosing said apparatus, said carrying case including a detachable wall having a rubber interior surface, adapted to be positioned in front and in alignment with the carriage plate, and a substrate detachably mounted on said rubber surface, said roller engaging said substrate.

* * * * *